(12) United States Patent
Buckingham et al.

(10) Patent No.: US 8,069,747 B2
(45) Date of Patent: Dec. 6, 2011

(54) ROBOTIC ARMS WITH COAXIALLY MOUNTED HELICAL SPRING MEANS

(75) Inventors: Robert Oliver Buckingham, Abingdon (GB); Andrew Crispin Graham, Bristol (GB)

(73) Assignee: Oliver Crispin Robotics Limited (GB)

( * ) Notice: Subject to any disclaimer, the term of this patent is extended or adjusted under 35 U.S.C. 154(b) by 0 days.

(21) Appl. No.: 12/168,624

(22) Filed: Jul. 7, 2008

(65) Prior Publication Data

US 2009/0012648 A1 Jan. 8, 2009

Related U.S. Application Data

(63) Continuation of application No. PCT/GB2007/000034, filed on Jan. 8, 2007.

(30) Foreign Application Priority Data

Jan. 6, 2006 (GB) .................................. 0600170.5

(51) Int. Cl.
  *B25J 17/00* (2006.01)
(52) U.S. Cl. ........................... 74/490.04; 901/15; 901/21
(58) Field of Classification Search .................... 74/469, 74/479, 490.01, 490.04, 490.05, 479.01; 901/15, 21, 28, 29
  See application file for complete search history.

(56) References Cited

U.S. PATENT DOCUMENTS

| | | | | |
|---|---|---|---|---|
| 2,761,297 A | * | 9/1956 | Buchsteiner | 464/53 |
| 3,266,059 A | * | 8/1966 | Stelle | 623/62 |
| 3,456,514 A | * | 7/1969 | Gebendinger | 74/110 |
| 4,621,965 A | * | 11/1986 | Wilcock | 414/7 |
| 5,297,443 A | * | 3/1994 | Wentz | 74/490.04 |
| 6,254,592 B1 | * | 7/2001 | Samson et al. | 606/1 |
| 2004/0138700 A1 | * | 7/2004 | Cooper et al. | 606/205 |

FOREIGN PATENT DOCUMENTS

| | | |
|---|---|---|
| EP | 1224904 | 7/2002 |
| JP | 2005271145 | 10/2005 |
| WO | 0216995 A3 | 2/2002 |
| WO | 02100608 A1 | 12/2002 |

OTHER PUBLICATIONS

International Search Report and Written Opinion, Apr. 19, 2007, 11 pages.
International Preliminary Search Report, Mar. 31, 2008, 7 pages.

\* cited by examiner

*Primary Examiner* — James Pilkington
(74) *Attorney, Agent, or Firm* — St. Onge Steward Johnston & Reens LLC

(57) ABSTRACT

A robotic arm comprising a plurality of segments, each comprising articulated links, and means for causing each segment to bend so the arm can follow a serpentine path. A helical spring is provided coaxially with the arm to urge the links to an initial datum position, and to distribute the bending over the links of each segment.

28 Claims, 7 Drawing Sheets

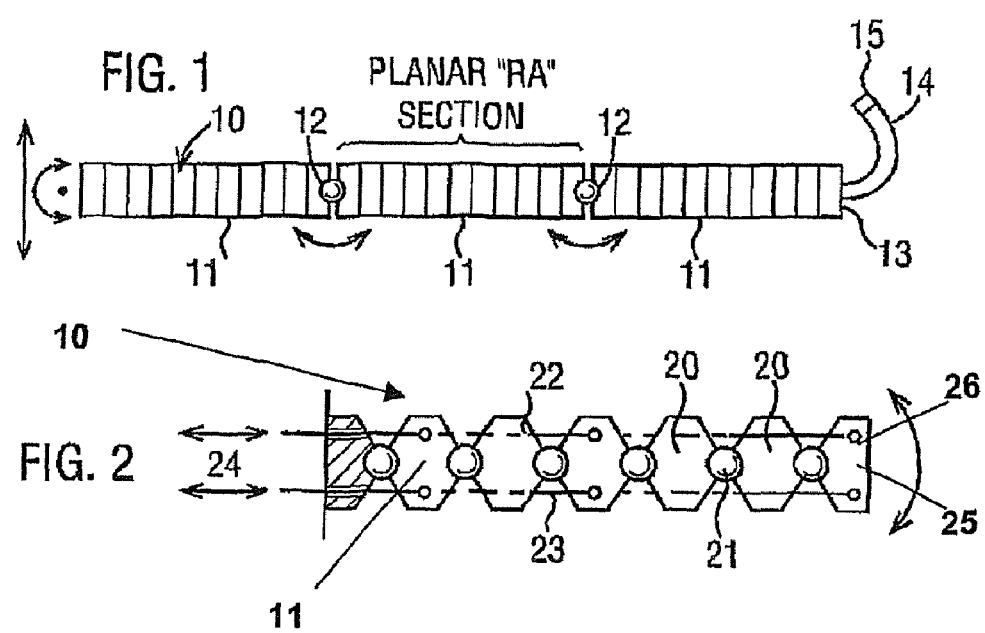
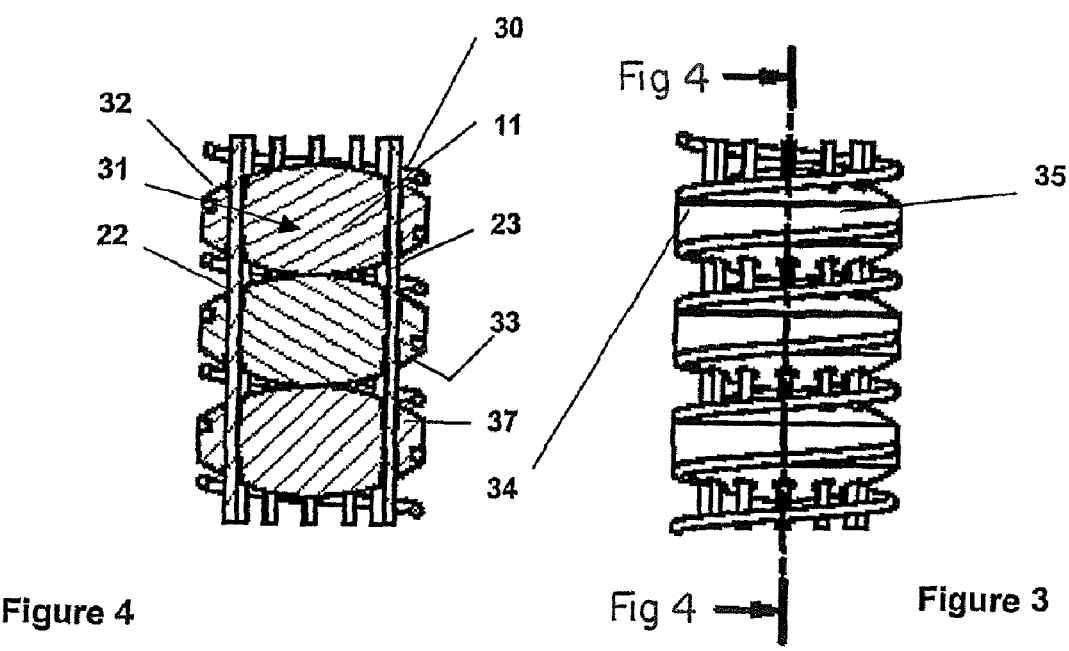

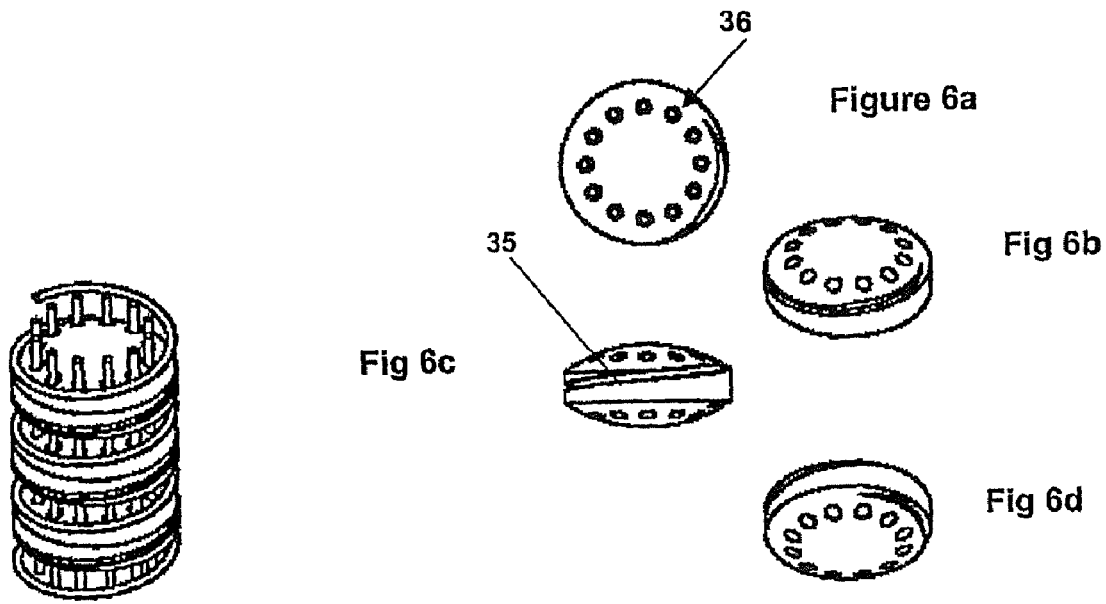
Figure 5
Figure 6a
Fig 6b
Fig 6c
Fig 6d
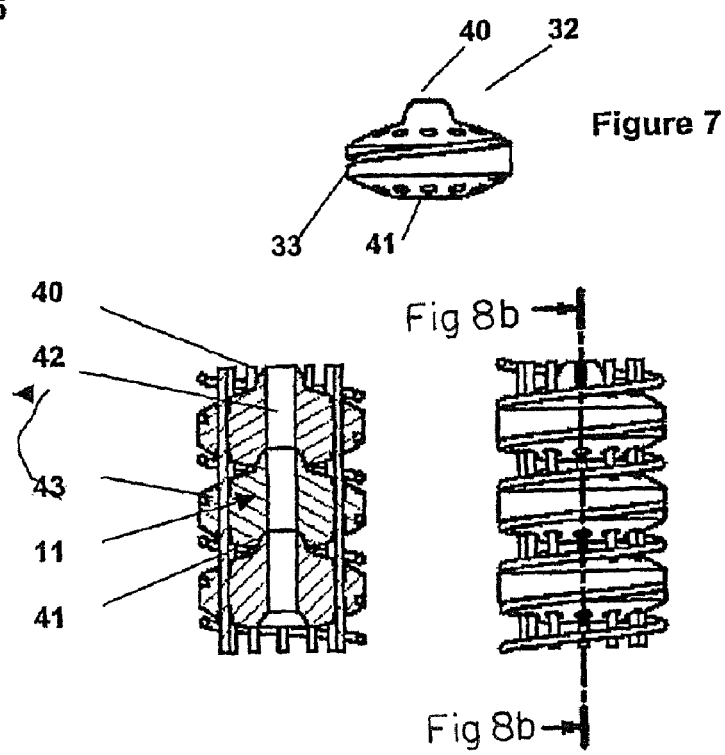
Figure 7
Figure 8b    Figure 8a

ROBOTIC ARMS WITH COAXIALLY MOUNTED HELICAL SPRING MEANS

CROSS-REFERENCE TO RELATED APPLICATIONS

The present application is a continuation of pending International patent application PCT/GB2007/000034 filed on Jan. 8, 2007 which designates the United States and claims priority from GB patent application 0600170.5 filed on Jan. 6, 2006, the content of which is incorporated herein by reference.

FIELD OF THE INVENTION

This invention relates to robotic arms, and has particular reference to a robotic arm having one or more controllable segments of which comprises a plurality of links, each of which links is articulated with respect to its neighbour thereby allowing each segment to bend.

BACKGROUND OF THE INVENTION

Our co-pending application WO02/016995, the disclosure of which is incorporated herein by reference, describes and claims such an arm. The arm has a work head adapted to carry a tool or examination element for work or examination at a site, and operating means for operational control of the work head. The arm is adapted to be able to reach the site in a 'tip following' manner to position the work head in a desired operating position. This is achieved with control means controlling the position and/or attitude of each arm segment relative to a datum thereby enabling the arm to follow and adapt to a predetermined path.

Robotic arms of this type may be referred to as "snake arms", since they have the ability to advance longitudinally along their own length thus enabling them to follow a serpentine path. This has the advantage that arms of this type may be used in circumstances where access to a work site is severely restricted.

For example, in some such snake arms, the articulation of the links in each segment may be controlled with precision to enable the arm to follow a convoluted path to guide a work tool into, for example, a restricted access pathway within a machine or a lumen of the human body.

Such a construction, however, requires precision engineering of each component to minimise frictional losses at the point of articulation between each pair of links. In a multi-link segment arm, these friction losses build up and the overall friction losses to be overcome during manipulation of the arm can be considerable. There is a need, therefore, for a device in which the manufacture of the components is relatively straightforward and in which the friction losses are significantly reduced.

In the arm forming the subject of WO02/016995, each segment is controlled by driven control cables terminating at the distal end of the segment. Springs are provided to bias each of the links against the compressive force exerted by the control cables in order to reduce friction. While successful in achieving its object, this further adds to the complexity of the system and hence to the complexity and cost of manufacture.

An alternative approach is set out in our co-pending application WO02/100608, the disclosure of which is also incorporated herein by reference, which dispenses with the springs and interposes instead a layer of rubber or elastomeric material either bonded or keyed to the two members constituting the articulation between adjacent links within a segment, the rubber providing the resilient shear capacity necessary to produce "stiffness" of the joint. While this arrangement is eminently satisfactory, it does again add to the complexity of construction. The present applicants have found that by using at least one spring which is interconnected to the series of individual links within a segment, significant advantages accrue in terms of manufacturability, increased axial loading and torsional stiffness, and indeed increased options in the properties of the resultant arm.

SUMMARY OF THE INVENTION

According to the present invention, therefore, there is provided a robot arm comprising:—a plurality of longitudinal segments extending end-to-end to define a longitudinal axis of the arm wherein each segment comprises a plurality of links, each link being capable of articulation one relative to another; actuator means for a segment to control the shape thereof by causing or allowing the segment to bend by articulating between the links thereof; and control means for controlling the actuator means to cause or allow different segments along the arm to assume different or related shapes to define the desired spatial attitude of the arm; characterised by helical spring means mounted coaxially with the arm and engaging the links within a segment so as to cause or allow the links to tend to an initial datum position, and to distribute the articulation amongst the links of the segment.

Where the links within a segment are maintained under compression by actuator means such as control cables, the spring means may be arranged to apply tension to the links within the segment to reduce friction between the links while maintaining the torsional stiffness of the segment. Alternatively, the spring means may be arranged so as to maintain the links under compression in order to reduce the load in the actuator means and hold the arm together. In this case, the arm may retain its shape even when the actuator means does not exert a load on them.

The spring means may comprise a single spring, which is interconnected to each of the individual links within a segment. Alternatively, a plurality of springs may be employed each of which operatively interconnects with each of the links within the segment.

According to a further aspect of the present invention, there is provided a link assembly for the segment of a robot arm or snake arm, which comprises a plurality of links disposed longitudinally of the arm and each adapted for limited movement one with respect to the other, each of said links being fixed with respect to said spring means, the arrangement being such that the spring means may deform by bending.

In another aspect of the invention, the spring means may be a single spring extending the length of the segment to which each link is optionally fixedly attached. In a more specific aspect, the spring means may be a helical spring. Each link may be attached to a helix of the spring. Each link may be attached to the spring so that adjacent links are biased apart. The helical spring may be disposed externally about the link assembly for the segment.

In an alternative embodiment, the spring means may be disposed internally of the link assembly. It will be appreciated by the person skilled in the art that various combinations of springs may be used, for example, a plurality of springs may be provided externally of the links to provide an effective cladding for the arm, or a combination of internal springs and external springs maybe provided, the characteristics of each spring being selected so as to impart predetermined characteristics upon the arm. Thus, for example, by selecting a suitable combination of spring or springs the arm may adapt more readily to the particular purpose for which the arm is ultimately to be employed.

A spring is usually used in tension or compression. In one aspect of the present invention, the arrangement of links and the connection of the links constrain the spring such that it can only bend to form an arc. The links may be attached to the spring by suitable means, such, for example, as by the use of adhesive or by means of clamps or pins or by welding, or by mechanical key means.

In a preferred embodiment of the invention, the links may be provided with engagement means to enable the links to be sequentially rotationally engaged with the spring. Further, the links may be designed with a groove or series of teeth located on a helix to engage with the spring.

In another aspect of the invention, the unloaded pitch of the spring may be slightly longer or shorter than the pitch of the engagement means on the links so that as the links are sequentially rotationally engaged with the spring, the arrangement is such that the spring will urge adjacent links apart or together. If they are urged apart, this reduces any applied compressive load at the interface between adjacent links. If urged together, this helps to ensure that the links engage correctly during use. Should excessive force cause the links to disengage, the spring will cause them to re-engage on removal of the force, such that the arm is resilient to damage.

End cap means may be provided to engage with the first and last links of the segment and with the spring to ensure that the links are unable to rotate with respect to the spring.

In one embodiment of the invention, adjacent links within a segment may be articulated one with respect to the other so that the segment may bend rather in the manner of a tightly strung row of beads. The means of articulation may be any suitable technique known to the person skilled in the art. Such articulation means however should preferably make provision for the supply of services along the segment and for the provision of the articulation and control means for the segment.

The articulation means may further constrain the degrees of freedom between adjacent links so as to limit the modes of deformation of the segments only to arcuate bending in response to operation of the actuation means. In one aspect of the invention, the articulation may be a simple ball- and socket joint which will allow the segments to bend one with respect to the other. The articulation may incorporate means for securing one link with respect to the other. In an alternative embodiment, this securing feature may be dispensed with and the retention of the links within the segment structure may be by means of the said spring means and/or by means of the tension means.

The spacing of the points of attachment of adjacent links along the helix of the spring will clearly affect the flexibility of the finished arm. It will be appreciated by a person skilled in the art that there is a relationship between the inclination of the helix to the longitudinal axis of the segment and the resultant flexibility of the finished arm.

In general, it is preferred that there should be approximately one or more complete wraps or coils of the helix of the spring between attachment points on adjacent links. Shortening this, results in an arm with a reduced ability to bend, while lengthening it increases the potential flexibility. The person skilled in the art will further appreciate that if substantially less than one complete coil or wrap of spring is free to move between adjacent links, the helix may be over-constrained and may experience substantially higher stresses than if at least one complete coil of the spring is free to move between the attachment point on adjacent links.

Variable tension or compression characteristics may be imparted to the segment by employing spring means having a different pitch along its length in order to vary the pre-tension or pre-compression in the spring once the links are inserted. Alternatively, the spring may be of constant pitch and the pitch of the engagement means on the link may be different in order to vary the pretension in the spring once the links are inserted. Such variation of pre-tension or pre-compression may be used to advantage in the design of the articulation between adjacent links.

The invention provides for control means for the arm as described in our prior applications acknowledged above the disclosure of the specifications of which are incorporated herein by reference.

In a typical embodiment, three wires may be provided for the control of each segment. Each wire is attached to an actuator and extends from one end of the segment to the other, whereby operating the actuators to change the tension in the wires one relative to the other, causes or allows the links to flex thereby controlling the movement and shape of the segment. The application of differential tension between the wires causes or allows the segment to move or bend. Control means for the actuators may include software to cause or allow movement of the arm in a predetermined manner.

In another aspect of the present invention, the robotic arm may have one continuous spring. Alternatively, each segment may have a separate spring of different characteristics.

In another feature of the present invention, a second spring concentric to the first spring may be provided and held in tension or in compression so that the links are both constrained by the first spring and the second spring.

In yet another embodiment of the present invention more than one spring may be used. In a particular aspect, three springs of the same diameter may be used with each link attached to all three springs, for example, by means of simple pins through holes in the springs.

In another embodiment, three or more springs of the same diameter may be used with each link attached to all of the springs by any of the means herein described. In another embodiment, combinations of two or more differently handed springs or sets of springs of equal diameter may be used with each link attached to all of the springs such that the rotary movement of a link with respect to one spring would result in a change in tension or compression in another spring, said change in tension serving to constrain further rotary movement of the links one with respect to another.

The present invention enables the undoubted benefits of the "snake arm" to be incorporated in much smaller devices, which are therefore capable of working in a much more restricted environment. Furthermore, the arm construction in accordance with the present invention permits of a more simplified structure than hitherto thus enabling more rapid and simplified construction and hence a significant reduction in cost.

Another advantage is the ability of the spring to provide support for a cover or sheath for the device, or to provide the basis of an internal conduit for services or cables rooted through the centre of the device. There is an increasing need to provide a cover for arms in accordance with the invention to isolate the arm structure from the surroundings in which it operates. The nature of such a cover or "skin" will depend on the environment in which the arm is used. In a further embodiment of the invention, the skin may incorporate the spring means either to replace the spring per se as described above or to supplement its effect.

A further embodiment of the invention will permit the spring to be of the non-metallic variety, such as from a plastics material. This will permit for a non-metallic construction of the arm.

Following is a description by way of example only and with reference to the accompanying informal drawings of methods of carrying the invention into effect.

BRIEF DESCRIPTION OF THE DRAWINGS

FIG. 1 is a diagrammatic representation of a prior art segmented arm to which this invention relates.

FIG. 2 is a diagrammatic representation of a segment of the arm of FIG. 1.

FIG. 3 is a side view of a portion of a segment of an arm in accordance with the present invention. FIG. 4 is a section along the line A-A of FIG. 3.

FIG. 5 is a perspective view of FIG. 3.

FIG. 6a, b, c, and d are detailed views of a link of the arm of FIGS. 3, 4 & 5.

FIG. 7 is a side view of a modified link for the arm of a FIG. 3.

FIG. 8a is a side view of part of the segment of an arm in using the links of FIG. 7.

FIG. 8b is a section along the line A-A of FIG. 8a.

FIGS. 9a, 9b, 9c. & 9d are detailed views of an alternative link construction in accordance with the present invention.

FIG. 10b is a section along the line A-A of FIG. 10a.

FIG. 11b is a perspective view of a link of the part segment of FIG. 11a.

FIG. 11c is a side view of FIG. 11a.

FIG. 12b constitutes two perspective views of a link for use in FIG. 12a.

FIG. 12c is a side view of FIG. 12a.

FIG. 13b is a side view of a link for use in FIG. 13a. FIG. 13c is a side view of FIG. 13a.

FIG. 14b is a perspective view of a link for use in the part segment of FIG. 14a.

FIG. 14c is a side view of FIG. 14a.

DETAILED DESCRIPTION OF THE INVENTION

Figure 10B:
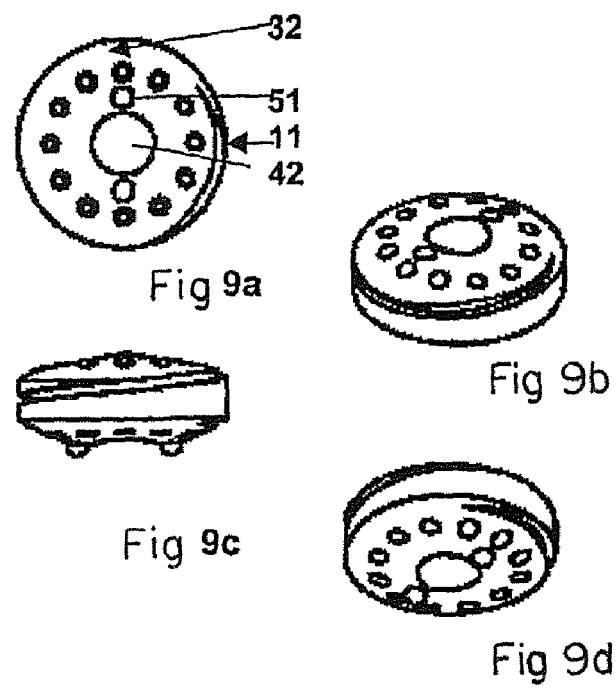

Referring to FIGS. 1 & 2, the arm as shown comprises three segments 10, each segment 10 comprising a plurality of link elements 11. Each segment 10 is connected to its neighbour by means of an articulated joint 12. The distal end 13 of the arm carries a work head 14 incorporating a tool 15. Each plurality of link elements may comprise an end cap 11' to engage with the first and last links of the segment and with the spring to contain rotation of the links with respect to the spring.

Each individual link 11, is capable of limited movement with respect to its neighbour by virtue of an articulated joint 21 (see FIG. 2) and the segment 10 as a whole is controlled by means of control wires and 22 and 23 which extended through each of the intermediate links 11 and is fixedly attached to the end element 25 of segment 10. Each of the control wires extends to actuator means indicated generally at 24 in FIG. 2, which actuator means can be controlled to provide varying tensions to each of the control wires. In normal operation, each of the control wires 22 and 23 are maintained under slight tension so as to apply a slight compressive force to the articulated link joint 21. In order to cause the segment to move the appropriate actuator means applies increased tension to the upper control wire 22, and increased force is applied to the upper attachment point 26 of the end element 25 which causes the end element to move upwardly and hence the arm to bend upwards relative to its datum position. It will be appreciated by the person skilled in the art that by providing three control wires it will be possible to obtain movement of the arm in any of the three dimensions provided there is suitable freedom of movement by the articulated link joints 21.

Turning now to the present invention, which is shown in a simple version shown in FIGS. 3 to 6, the individual links 11 are surrounded by a single continuous wire helix 30 with the control wires 23 and 22 passing through the link as before. Each link 11 is in the form of a disk 31 having a generally convex upper surface 32, a similar convex lower surface 33, and a generally cylindrical edge 34 incorporating a helical groove 35.

As will be apparent from FIG. 6a, disk 31 is provided with circumferentially spaced, axially aligned holes 36 each adapted to accommodate a control wire. These holes are fluted towards the upper and lower ends so that each hole increased slightly in diameter towards the exit. In the specific example illustrated there are 12 holes 36 allowing for the control wires for a four-segment arm.

As can be seen from FIG. 4, the convex surfaces of 32 and 33 are adapted to abut the corresponding surface of the next adjacent link and constitute bearing surfaces to maintain the link spacing. Such a bearing arrangement between links has no torsional constraint and in this case increasing tension in wires 23, 24 will provide increased torsional stiffness.

The external helical groove 35 is adapted to accommodate helical spring 37 which may optionally be fixedly attached to the link 11 by means of pins, adhesive or other appropriate means. The attachment of the helical spring 37 to the external surface of the disk 11 may be effected in such a way as to provide, in the rest position of the arm with no tension applied to the control wires, a slight spacing between adjacent discs 11 so that when tension is applied to the control wires 22, 23, the external helical spring 37 seeks to bias apart adjacent links 11.

In an alternative embodiment, the links may be attached to the helical spring 37 such that the spring, in the rest position, is already under tension to urge the links 11 together and to maintain them under a compressive force.

In the particular embodiment of FIGS. 3 to 6, there is no constraint on shear applied to the links within a segment except the constraint applied by the tension in the control wires 22, 23 so that the links can be shifted laterally in relation to each other with no ready means of recovering that shear offset. Furthermore, the provision of a central bore is not practicable, since the entire convex surface of the disk is used as a bearing.

A modified link is shown in FIG. 7. This is similar to that of the FIGS. 4 to 6 except that it is provided with a projecting ball portion 40 in upper convex surface 32 and a socket 41 in the underside of surface 33 adapted to receive the ball portion 40 of the next adjacent link element 11a. In this case, each link element 11 is provided with a central bore 42 extending from the base of the socket 41 up to the extremity of the ball 40. As will be apparent from the FIG. 8b, the bore 42 of adjacent link 11 within the segment will provide a continuous conduit or duct for the provision of services along the length of the arm.

The size of the ball and socket arrangement and hence the size of the central conduit 42 will be determined to a large extent by the desired degree of relative movement between one link and its neighbour and the number of wires to be provided for controlling the length of the arm. Again, the bearing between the links has no torsional constraint and this is another instance where an increase in the wire tension will increase the torsional stiffness of the device.

Compared with the example of FIG. 5 above, the problem of shear constraint has been overcome by the lateral constraint provided by the ball and socket. Where an arm of relatively large diameter is to be considered, then the frictional forces of such a ball and socket arrangement tend to increase and this reduces the tendency of the segments to assume a truly arcuate form in use. It should be noted that holes 36 accommodating the actuator wires or ropes 23, 24 are fluted at 43 towards each end to allow for the ease of passage of the wires within the bores when the links 11 are inclined at an angle one with respect to the other.

Figure 10A:
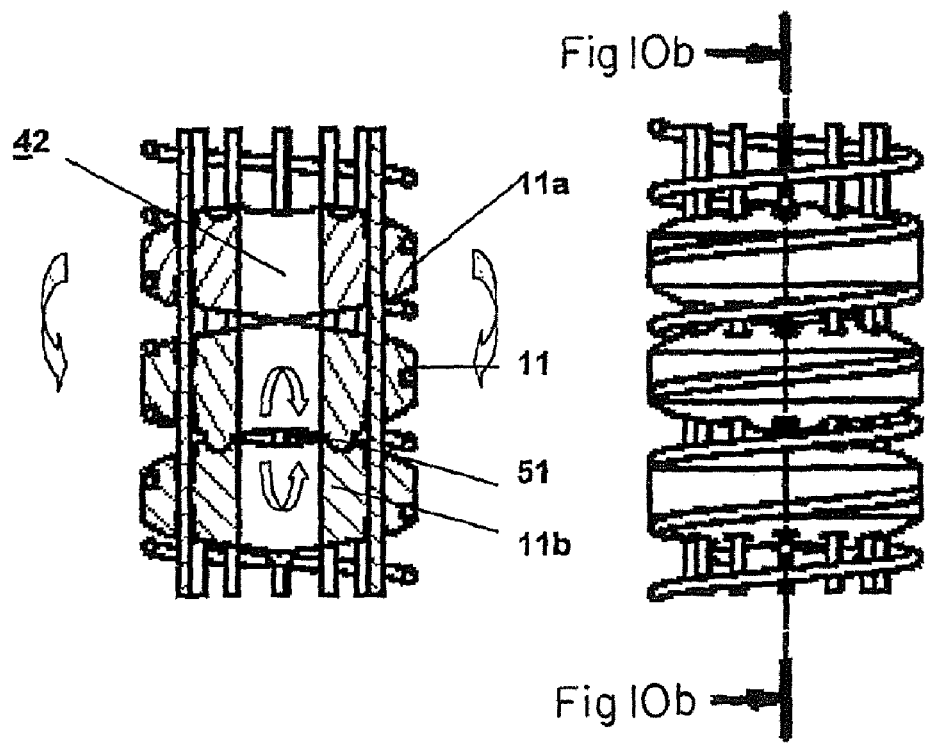
FIG. 10a is a side view of part of a segment incorporating the links of FIG. 9.
Figure 11A:
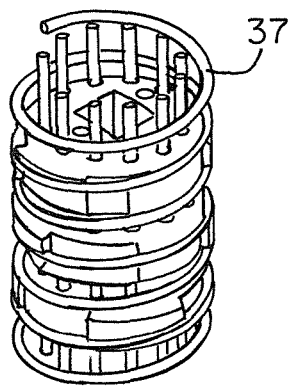
FIG. 11a is a perspective view of part of a segment of a further embodiment of the invention.
Figure 11B:
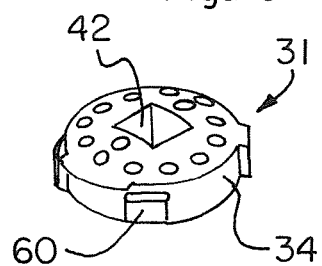
Figure 11D:
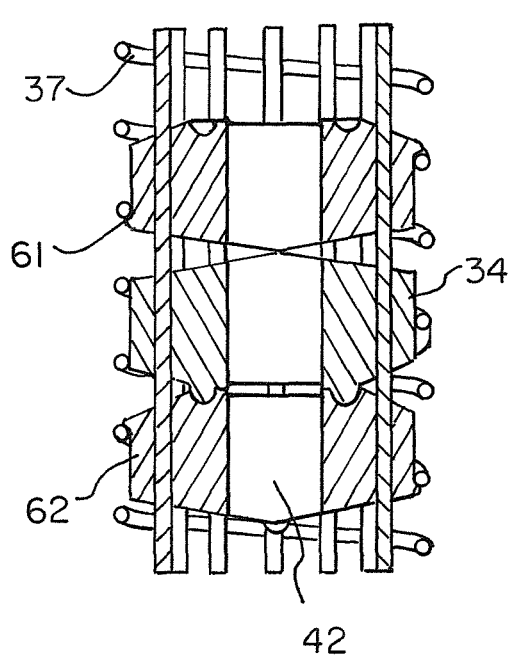
FIG. 11d is a section on the line A-A of FIG. 11c.
Figure 11C:
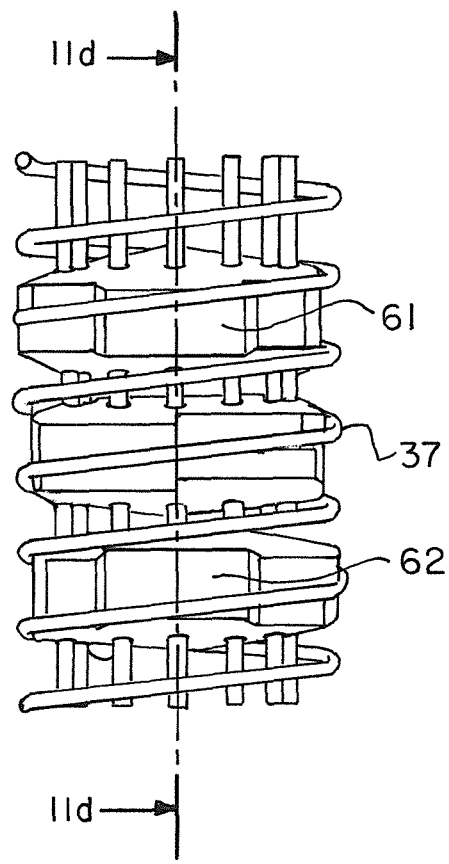
Figure 12A:
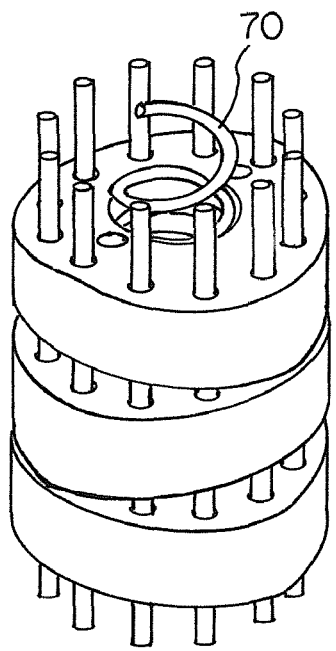
FIG. 12a is a perspective view of a part segment showing the incorporation of a spring internally of the link assembly.
Figure 12B:
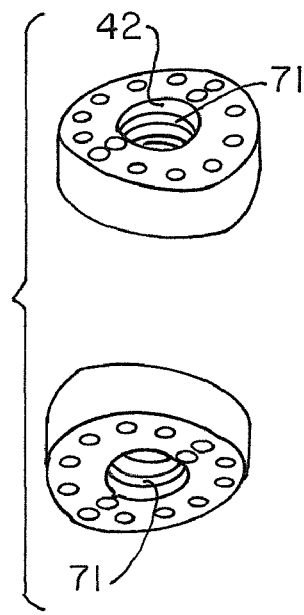
Figure 12D:
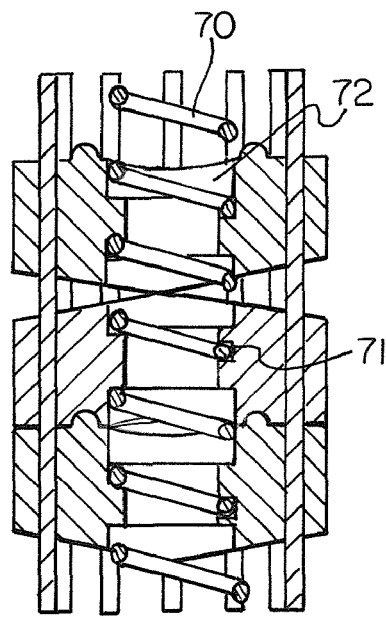
FIG. 12d is a section along the lines A-A of FIG. 12c.
Figure 12C:
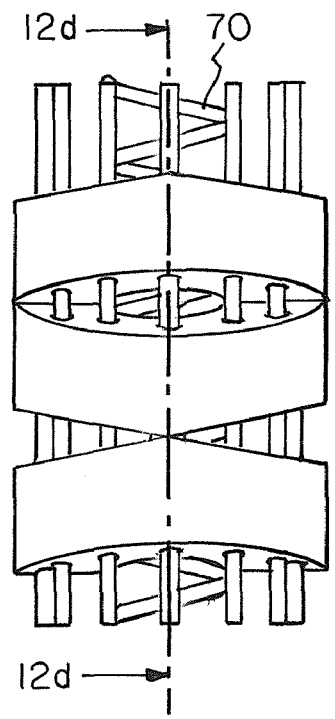
Figure 13B:
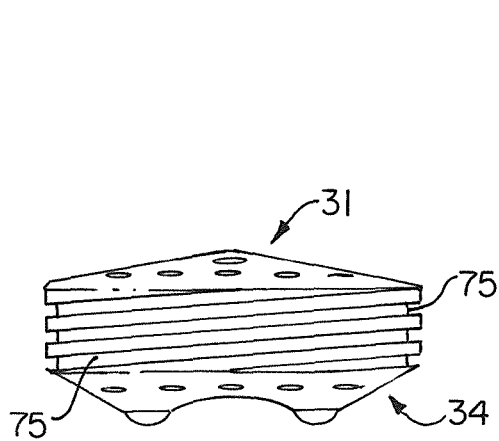
Figure 13A:
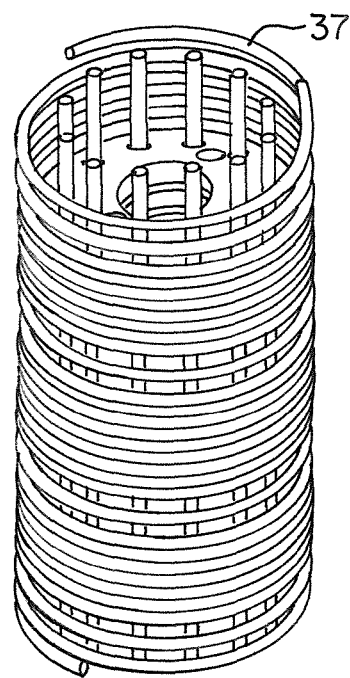
FIG. 13a is a perspective view of a multi spring assembly.
Figure 13D:
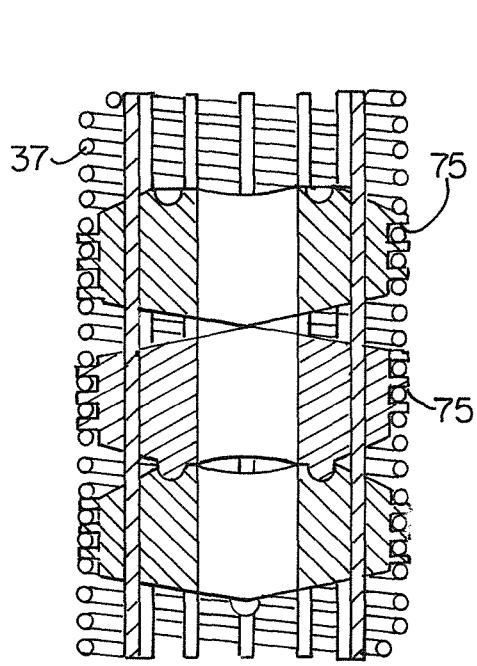
FIG. 13d is a section of along the line A-A of FIG. 13c.
Figure 13C:
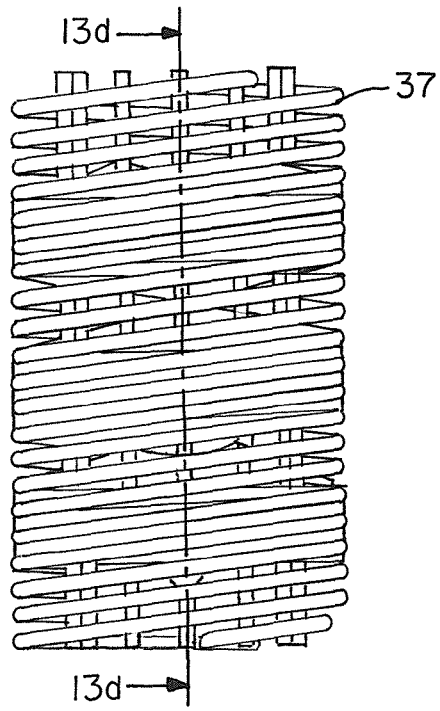
Figure 14A:
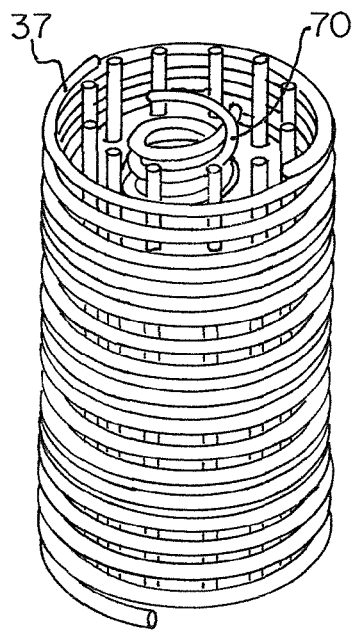
FIG. 14a is a perspective view of a part segment showing the use of both internal and external spring assemblies.
Figure 14B:
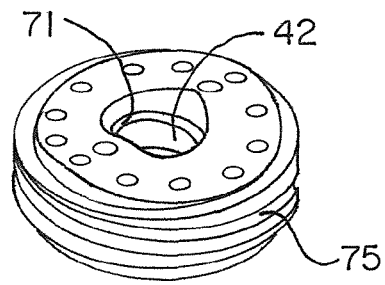
Figure 14D:
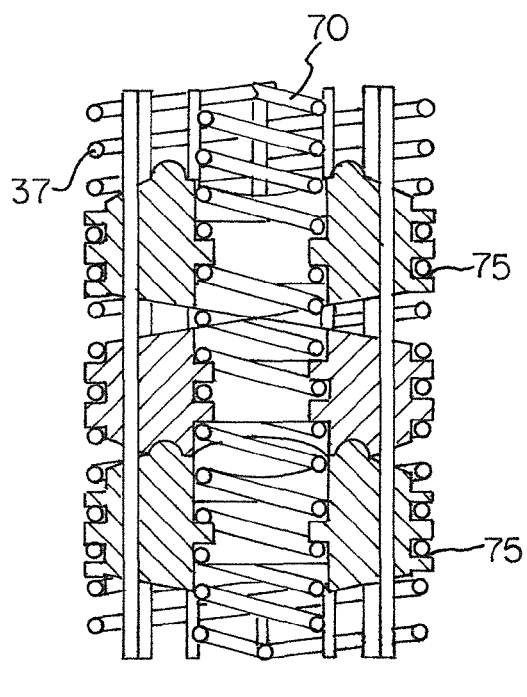
FIG. 14d is a section along the line A-A of FIG. 14c.
Figure 14C:
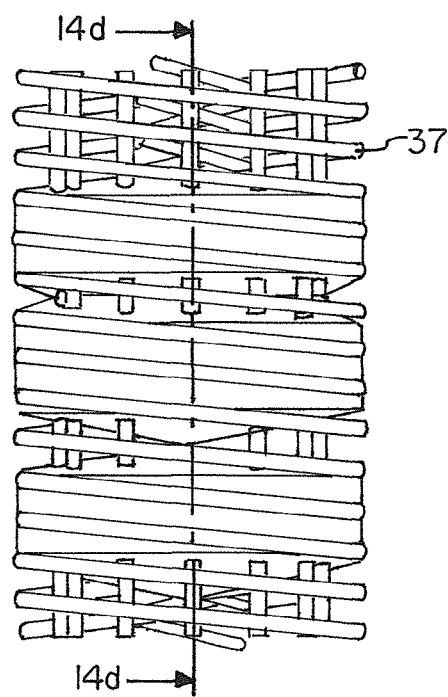

A further modification of each link element 11 is shown in FIGS. 9 and 10 in which each link element is provided with a central bore 42 as previously described and the lower convex surface 33 is provided with a pair of diametrically spaced balls 50. The upper convex surface 32 is provided with a pair of corresponding depressions 51 disposed on a diameter substantially at right angles to the diameter containing the balls 50 on the lower convex surface 33. When assembled as shown in FIG. 10b, the balls 50 on one link 11 engage with the depressions 51 on the upper surface of the adjacent link. As before, the central bores 42 will align or correspond to provide a central conduit. In this case, however, the relative angles of the ball and depression bearings will allow movements or bending motion between the adjacent links in only one plane in the manner of a hinge. The next link 11a in FIG. 10b will hinge at right angles to the plane containing the hinge of the links 11, lib. In this way, the full flexibility of the arm is preserved while the ball and socket arrangement provides torsional constraint so the torsional stiffness of this assembly is not affected by wire tension. It will be appreciated that the size of the central bore in this case is limited only by the separation between the balls 50 and the corresponding depressions 51. Furthermore, the balls 50 and their corresponding depressions or sockets 51 can be chosen to be as small as possible (depending upon the loads they are required to accommodate) which has the effect of minimising friction at the hinge positions. The joints between links in the assembly as illustrated have only one degree of freedom in that they are a hinge, so alternate joints are disposed at an angle to each other. This angular disposition need not necessarily be a right angle. By providing angular spacing in this way the segment can bend with several degrees of freedom. In an alternative embodiment of the invention, the hinge joints may be aligned to obtain a segment with only a single degree of freedom which would be suitable for planar applications only.

The embodiment illustrated in FIG. 11 is a modification of that described with respect to FIG. 10. In this embodiment, the cylindrical surface or edge 34 of disk 31 is provided with a plurality of circumferentially spaced lugs 60 each of which is configured to provide a shelf or engagement to define a path to receive helical spring 37. The lugs 60 provide an upwardly facing shelf 61 juxtaposed but circumferentially spaced from a downwardly- facing shelf 62, the surface of which shelf is adapted to bear against a surface of part of helical spring 37.

The arrangement of lugs and shelves is such to define a helical path about the external cylindrical surface 34 of disk 31 so that the spring 37 can snap between the lugs 60 and shelves 61 and 62. The spring can, once again, be optionally fixedly secured to the disk 31 by means of pins, adhesive or any other suitable fastening means. The unloaded pitch 37' of the spring may be slightly longer or shorter than the pitch 61' of the engagement member on the links so that as the links are sequentially rotationally engaged with the spring, the arrangement is such that the spring will urge adjacent links apart or together. If they are urged apart, this reduces any applied compressive load at the interface between adjacent links. If urged together, this helps to ensure that the links engage correctly during use. Should excessive force cause the links to disengage, the spring will cause them to re-engage on removal of the force, such that the arm is resilient to damage. The spring may have a different pitch at different positions (60', 60", 60''') along its length in order to vary the pre-tension or pre-compression in the spring.

In this embodiment, the central bore 42 is of generally square cross-section the size of which is limited only by the separation between the balls and depressions, and as before the joints between adjacent links have only one degree of freedom. This arrangement allows for ease of moulding and enables components to be readily manufactured by injection moulding from plastics materials.

The embodiment described with respect to FIG. 12 is a variation on the foregoing in that the spring on this occasion is an internal spring 70. To accommodate this, the central bore 42 is of generally circular cross-section and is provided with an internal groove 71 to receive and locate the spring 70. The central bore 42 is additionally provided towards each end with a portion of wider diameter 72 at each end thereof to allow for movement or flexing of the spring as the links 11 bend one with respect to the other. The single internal groove 71 may be machined or produced by a complex casting or injection moulding. As before each link element 11 may be secured to the spring in the manner described above.

The FIG. 13 illustrates an embodiment in which multiple springs and may be employed. In this case the cylindrical edge of 34 of disk 31 is provided with multiple grooves or lands 75 each of which is adapted to receive the helix of a helical spring 37. In the example shown, three identical helical springs 37 may be employed each fixed into the grooves 75 as described above. Alternatively, the springs may be may have differing properties to impart different characteristics upon the segment. An aspect of the invention envisages an arm construction having a plurality of segments, each segment of which has properties different from its neighbour.

Turning now to the embodiment of FIG. 14, this construction has a combination of an internal spring 70 and a plurality of external helical springs 37. The basic construction of each of the link elements 11 is identical, with a central bore 42 having a helical groove as generally described with respect to FIG. 12 above. The advantage here is that the handing of the helical springs can be different and the combination of the left-handed and right-handed spring sets assist in maintaining the assembly during use, for example, if in operation, one of the spring sets starts to "wind up" this action will be opposed by the other spring(s).

In the assembly of the device of FIG. 14, it is essential that the links are screwed firstly onto the internal spring 70 and the external spring or springs 37 is then subsequently applied.

It will be appreciated by the person skilled in the art that the individual links within the each segment will be identical. By providing only one degree of freedom between adjacent links, no additional moving parts will be necessary and the necessary tension can be applied by a combination of spring(s) and tension in the operating wires or ropes. The construction of an arm in this way, therefore, becomes relatively simple and the extensive machining of components can be reduced to a minimum. Furthermore, in operations where the link elements 11 can be of a plastic material, it is envisaged that this construction will permit the use of injection moulded components. The invention provides, therefore, for a significantly cheaper method of producing a "snake arm" than heretofore and furthermore, permits the production of arms of different properties which can be readily interchangeable for any given actuator array and control system.

What is claimed is:

1. A robot arm comprising:
a plurality of longitudinal segments extending end-to-end to define a longitudinal axis of the arm wherein each segment comprises a plurality of links connected by articulated joints;
an actuator for a segment to control the shape thereof by causing or allowing the segment to bend by articulating between the links thereof;
a controller for controlling the actuator to cause or allow different segments along the arm to assume different or related shapes to define the desired spatial attitude of the arm;
characterized by at least one spring mounted coaxially with the arm and engaging with an engagement member on each of the links within a segment so as to cause the links to tend to an initial datum position, and to distribute the articulation amongst the links of the segment, in which the at least one spring is fixedly attached to each of the links by the engagement member along the longitudinal axis, the arrangement being such that the at least one spring may deform by bending to form an arc;
wherein the at least one spring engages with the engagement member along a helical path with respect to each of the links.

2. A robot arm as claimed in claim 1, in which the actuator is arranged to apply a compressive force to the links within a segment, and in which the at least one spring is arranged to apply tension to the links within the segments to reduce friction between links within said segment while maintaining a torsional stiffness.

3. A robot arm as claimed in claim 1, in which the at least one spring comprises a plurality of springs each of which operatively interconnects with each of the links within the segment.

4. A robot arm as claimed in claim 1, wherein the engagement members enable the links to be sequentially rotationally engaged with the at least one spring.

5. A robot arm as claimed in claim 4, comprising an end cap to engage with a first and a last link of the segment and with the at least one spring to contain rotation of the links with respect to the at least one spring.

6. A robot arm as claimed in claim 1, in which each link comprises a groove or series of teeth located on a helix to engage with the at least one spring.

7. A robot arm as claimed in claim 6, in which an unloaded pitch of the at least one spring is longer or shorter than a pitch of the engagement member on the links so that as the links are sequentially rotationally engaged with the at least one spring, the at least one spring is pre-tensioned or pre-compressed respectively, so as to urge adjacent links apart or together respectively.

8. A robot arm as claimed in claim 7, in which the spring has a different pitch at different positions along its length in order to vary the pre-tension or pre-compression in the at least one spring.

9. A robot arm as claimed in claim 7, in which the pitch of the engagement member on the different links is different in order to vary the pretension or pre-compression.

10. A robot arm as claimed in claim 1, in which the at least one spring is disposed externally about the links.

11. A robot arm as claimed in claim 1, in which the spring is disposed internally of the link assembly.

12. A robot arm as claimed in claim 1, in which the at least one spring comprises a plurality of springs.

13. A robot arm as claimed in claim 1, in which the arrangement of links and the connection of links constrain the at least one spring such that it can only bend to form an arc.

14. A robot arm as claimed in claim 1, in which the links are attached to the at least one spring by adhesive or by means of clamps or pins or by welding, or by mechanical key means.

15. A robot arm as claimed in claim 1, in which the links are arranged to constrain the degrees of freedom between adjacent links so as to limit the modes of deformation of the segments only to arcuate bending in response to operation of the actuator.

16. A robot arm as claimed in claim 15, in which the articulated joint is a ball and socket joint.

17. A robot arm as claimed in claim 15, in which the articulation between adjacent links is arranged to allow bending movement in only one plane in the manner of a hinge.

18. A robot arm as claimed in claim 17, in which the articulation between adjacent links are disposed at an angle with respect to each other.

19. A robot arm as claimed in claim 17, in which the articulation comprises a projection on the surface of one link arranged to engage with a corresponding depression on the surface of the adjacent link.

20. A robot arm as claimed in claim 1, in which there is approximately at least one complete wrap or coil of the at least one spring between engaging points on adjacent links.

21. A robot arm as claimed in claim 1, in which the actuator comprises three control wires for the control of each segment.

22. A robot arm as claimed in claim 21, in which each wire is attached to an actuator and extends from one end of the segment to the other, whereby operating the actuators to change the tension in the wires, causes or allows the links to flex thereby controlling the movement and shape of the segment.

23. A robot arm as claimed in claim 1, in which the at least one spring comprises one continuous spring along the length of the arm.

24. A robot arm as claimed in claim 1, in which each segment has a separate spring, the separate springs having different characteristics.

25. A robot arm as claimed in claim 1, in which the at least one spring comprises a first spring and a second spring concentric to the first spring and held in tension or in compression so that the links are constrained by both the first spring and the second spring.

26. A robot arm as claimed in claim 1, in which the at least one spring comprises two springs of the same diameter, each link engaging the springs.

27. A robot arm as claimed in claim 1, in which the at least one spring comprises a combination of two or more differently handed springs, with each link attached to all of the springs such that the rotary movement of a link with respect to one spring would result in a change in tension or compression in another spring, said change in tension serving to constrain further rotary movement of the links with respect to one another.

28. A robot arm as claimed in claim 1, in which the engagement member is selected from the group consisting of: a groove, a series of teeth, an adhesive, clamps, pins, a weld, a mechanical key and combinations thereof.

* * * * *